US008000766B2

(12) United States Patent
Lang et al.

(10) Patent No.: US 8,000,766 B2
(45) Date of Patent: Aug. 16, 2011

(54) METHODS TO DIAGNOSE TREAT AND PREVENT BONE LOSS

(75) Inventors: Philipp Lang, Lexington, MA (US); Claude Arnaud, Mill Valley, CA (US); Daniel Steines, Lexington, MA (US)

(73) Assignee: ImaTx, Inc., Burlington, MA (US)

( * ) Notice: Subject to any disclaimer, the term of this patent is extended or adjusted under 35 U.S.C. 154(b) by 1253 days.

(21) Appl. No.: 10/157,745

(22) Filed: May 28, 2002

(65) Prior Publication Data

US 2003/0015208 A1    Jan. 23, 2003

Related U.S. Application Data

(60) Provisional application No. 60/293,898, filed on May 25, 2001, provisional application No. 60/293,489, filed on May 25, 2001.

(51) Int. Cl.
*A61B 5/05* (2006.01)
*G06K 9/00* (2006.01)
(52) U.S. Cl. ......... 600/407; 600/411; 600/427; 382/128
(58) Field of Classification Search .................. 600/411, 600/427, 406; 382/128
See application file for complete search history.

(56) References Cited

U.S. PATENT DOCUMENTS

| | | |
|---|---|---|
| 2,274,808 A | 3/1942 | Rinn ............................... 250/69 |
| 3,924,133 A | 12/1975 | Reiss ............................ 250/408 |
| 4,012,638 A | 3/1977 | Altschuler et al. ............ 250/491 |
| 4,126,789 A | 11/1978 | Vogl et al. ...................... 250/505 |
| 4,233,507 A | 11/1980 | Volz ............................... 250/252 |
| 4,251,732 A | 2/1981 | Fried ............................... 250/479 |
| 4,298,800 A | 11/1981 | Goldman ................... 250/445 T |
| 4,356,400 A | 10/1982 | Polizzi et al. ................. 378/138 |
| 4,400,827 A | 8/1983 | Spears ........................... 378/207 |
| 4,593,400 A | 6/1986 | Mouyen ........................... 378/99 |
| 4,649,561 A | 3/1987 | Arnold ........................... 378/207 |
| 4,686,695 A | 8/1987 | Macovski ....................... 378/146 |
| 4,721,112 A | 1/1988 | Hirano et al. ................. 128/659 |
| 4,782,502 A | 11/1988 | Schulz ............................ 378/18 |
| 4,922,915 A | 5/1990 | Arnold ....................... 128/653 R |
| 4,956,859 A | 9/1990 | Lanza et al. ................... 378/157 |
| 4,985,906 A | 1/1991 | Arnold ............................ 378/18 |
| 5,001,738 A | 3/1991 | Brooks ........................... 378/170 |
| 5,090,040 A | 2/1992 | Lanza et al. ..................... 378/62 |
| 5,122,664 A | 6/1992 | Ito et al. ...................... 250/327.2 |
| 5,127,032 A | 6/1992 | Lam et al. ...................... 378/189 |
| 5,150,394 A | 9/1992 | Karellas ........................... 378/62 |
| 5,172,695 A | 12/1992 | Cann et al. ................... 128/653.1 |
| 5,187,731 A | 2/1993 | Shimura ........................ 378/207 |
| 5,200,993 A | 4/1993 | Wheeler et al. ................. 379/96 |
| 5,222,021 A | 6/1993 | Feldman et al. ......... 364/413.14 |
| 5,228,445 A | 7/1993 | Pak et al. ................... 128/660.01 |
| 5,235,628 A | 8/1993 | Kalender ....................... 378/207 |
| 5,247,934 A | 9/1993 | Wehrli et al. ............... 128/653.2 |
| 5,270,651 A | 12/1993 | Wehrli ........................... 324/308 |
| 5,271,401 A | 12/1993 | Fishman ....................... 128/654 |
| 5,320,102 A | 6/1994 | Paul et al. ................... 128/653.2 |
| 5,335,260 A | 8/1994 | Arnold ........................... 378/207 |
| 5,384,643 A | 1/1995 | Inga et al. ...................... 358/403 |
| 5,476,865 A * | 12/1995 | Panetta et al. .................. 514/369 |
| 5,493,593 A | 2/1996 | Müller et al. .................... 378/19 |
| 5,493,601 A | 2/1996 | Fivez et al. .................... 378/207 |
| 5,513,240 A | 4/1996 | Hausmann et al. ........... 378/170 |
| 5,521,955 A | 5/1996 | Gohno et al. .................... 378/18 |
| 5,537,483 A | 7/1996 | Stapleton et al. ............. 382/309 |
| 5,562,448 A | 10/1996 | Mushabac ..................... 433/215 |
| 5,565,678 A | 10/1996 | Manian ......................... 428/690 |
| 5,592,943 A | 1/1997 | Buhler et al. ............. 128/661.03 |
| 5,600,574 A | 2/1997 | Reitan ........................... 364/552 |
| 5,657,369 A | 8/1997 | Stein et al. .................... 378/208 |
| 5,673,298 A | 9/1997 | Mazess ........................... 378/54 |
| 5,687,210 A | 11/1997 | Maitrejean et al. ............. 378/57 |
| 5,769,072 A | 6/1998 | Olsson et al. .................... 623/18 |
| 5,769,074 A | 6/1998 | Barnhill et al. | |
| 5,772,592 A | 6/1998 | Cheng et al. .................. 600/407 |
| 5,852,647 A | 12/1998 | Schick et al. ................... 378/53 |
| 5,864,146 A | 1/1999 | Karellas ......................... 250/581 |
| 5,886,353 A | 3/1999 | Spivey et al. ............. 250/370.09 |
| 5,915,036 A | 6/1999 | Grunkin et al. ............... 382/132 |
| 5,917,877 A | 6/1999 | Chiabrera et al. ............. 378/53 |
| 5,931,780 A | 8/1999 | Giger ............................. 600/407 |
| 5,945,412 A | 8/1999 | Fuh et al. ...................... 514/176 |

(Continued)

FOREIGN PATENT DOCUMENTS

CA       2342344       3/2000

(Continued)

OTHER PUBLICATIONS

Bauer et al., "Biochemical Markers of Bone Turnover and Prediction of Hip Bone Loss in Older Women: The Study of Osteoporotic Fractures," *Journal of Bone and Mineral Research* 14:1404-1410 (1999).

(Continued)

*Primary Examiner* — Michael T Rozanski
(74) *Attorney, Agent, or Firm* — Sunstein Kahn Murphy & Timbers LLP

(57) ABSTRACT

Methods of diagnosing and preventing bone loss and/or enhancing bone formation are disclosed. The invention additionally provides methods of diagnosing a predisposition to bone loss. The methods mathematically combine the information provided by imaging tests with the information provided by biomarkers to provide an index value. The index value is used for diagnosis of bone diseases, and to assess the progress of treatment of bone diseases.

21 Claims, No Drawings

U.S. PATENT DOCUMENTS

| | | | | |
|---|---|---|---|---|
| 5,948,692 | A * | 9/1999 | Miyauti et al. | 436/501 |
| 6,029,078 | A * | 2/2000 | Weinstein et al. | 600/407 |
| 6,064,716 | A | 5/2000 | Siffert et al. | 378/53 |
| 6,077,224 | A | 6/2000 | Lang et al. | 600/437 |
| 6,108,635 | A | 8/2000 | Herren et al. | 705/2 |
| 6,156,799 | A | 12/2000 | Hartke et al. | 514/573 |
| 6,178,225 | B1 | 1/2001 | Zur et al. | 378/98.2 |
| 6,205,348 | B1 | 3/2001 | Giger et al. | 600/407 |
| 6,215,846 | B1 | 4/2001 | Mazess et al. | 378/62 |
| 6,226,393 | B1 | 5/2001 | Grunkin et al. | 382/128 |
| 6,246,745 | B1 | 6/2001 | Bi et al. | 378/54 |
| 6,248,063 | B1 | 6/2001 | Barnhill et al. | 600/300 |
| 6,249,692 | B1 | 6/2001 | Cowin | 600/407 |
| 6,252,928 | B1 | 6/2001 | MacKenzie | 378/54 |
| 6,285,901 | B1 * | 9/2001 | Taicher et al. | 600/410 |
| 6,289,115 | B1 | 9/2001 | Takeo | 382/130 |
| 6,302,582 | B1 | 10/2001 | Nord et al. | 378/207 |
| 6,306,822 | B1 | 10/2001 | Kumagai et al. | 514/7 |
| 6,315,553 | B1 | 11/2001 | Sachdeva et al. | 433/24 |
| 6,320,931 | B1 | 11/2001 | Arnold et al. | 378/56 |
| 6,377,653 | B1 | 4/2002 | Lee et al. | 378/54 |
| 6,411,729 | B1 | 6/2002 | Grunkin | 382/132 |
| 6,430,427 | B1 | 8/2002 | Lee et al. | 600/407 |
| 6,442,287 | B1 | 8/2002 | Jiang et al. | 382/128 |
| 6,449,502 | B1 | 9/2002 | Ohkubo | 600/407 |
| 6,463,344 | B1 | 10/2002 | Pavloskaia et al. | 700/98 |
| 6,501,827 | B1 | 12/2002 | Takasawa | 378/116 |
| 6,556,698 | B1 | 4/2003 | Diano et al. | 382/132 |
| 6,690,761 | B2 | 2/2004 | Lang et al. | 378/56 |
| 6,694,047 | B1 | 2/2004 | Farrokhnia et al. | 382/132 |
| 6,717,174 | B2 | 4/2004 | Karellas | 250/582 |
| 6,799,066 | B2 | 9/2004 | Steines et al. | 600/407 |
| 6,807,249 | B2 | 10/2004 | Dinten et al. | 378/54 |
| 6,811,310 | B2 | 11/2004 | Lang et al. | 378/169 |
| 6,824,309 | B2 | 11/2004 | Robert-Coutant et al. | 378/207 |
| 6,829,378 | B2 | 12/2004 | DiFilippo et al. | 382/128 |
| 6,835,377 | B2 * | 12/2004 | Goldberg et al. | 424/93.7 |
| 6,836,557 | B2 | 12/2004 | Tamez-Pena et al. | 382/128 |
| 6,895,077 | B2 | 5/2005 | Karellas et al. | 378/98.3 |
| 6,904,123 | B2 | 6/2005 | Lang | 378/54 |
| 6,934,590 | B2 | 8/2005 | Ogawa | 700/19 |
| 6,975,894 | B2 | 12/2005 | Wehrli et al. | 600/407 |
| 7,050,534 | B2 | 5/2006 | Lang | 378/54 |
| 7,058,159 | B2 | 6/2006 | Lang et al. | 378/54 |
| 7,120,225 | B2 | 10/2006 | Lang et al. | 378/54 |
| 7,184,814 | B2 * | 2/2007 | Lang et al. | 600/416 |
| 7,239,908 | B1 | 7/2007 | Alexander et al. | 600/427 |
| 7,245,697 | B2 | 7/2007 | Lang | 378/54 |
| 7,283,857 | B1 | 10/2007 | Fallon et al. | |
| 7,292,674 | B2 | 11/2007 | Lang | 378/54 |
| 7,379,529 | B2 | 5/2008 | Lang | 378/54 |
| 7,467,892 | B2 | 12/2008 | Lang et al. | 378/207 |
| 7,545,964 | B2 | 6/2009 | Lang et al. | 382/128 |
| 7,580,504 | B2 | 8/2009 | Lang et al. | 378/56 |
| 7,660,453 | B2 | 2/2010 | Lang | 382/132 |
| 7,664,298 | B2 | 2/2010 | Lang et al. | 382/128 |
| 7,676,023 | B2 | 3/2010 | Lang | 378/54 |
| 7,840,247 | B2 | 11/2010 | Liew et al. | |
| 2002/0067798 | A1 | 6/2002 | Lang | 378/54 |
| 2002/0087274 | A1 | 7/2002 | Alexander et al. | 702/19 |
| 2002/0159567 | A1 | 10/2002 | Sako et al. | 378/117 |
| 2002/0186818 | A1 | 12/2002 | Arnaud et al. | 378/165 |
| 2002/0194019 | A1 | 12/2002 | Evertsz | 705/2 |
| 2002/0196966 | A1 | 12/2002 | Jiang et al. | 382/132 |
| 2003/0015208 | A1 | 1/2003 | Lang et al. | 128/922 |
| 2003/0198316 | A1 | 10/2003 | Dewaele et al. | 378/54 |
| 2004/0106868 | A1 | 6/2004 | Liew et al. | 600/442 |
| 2004/0242987 | A1 | 12/2004 | Liew et al. | 600/407 |
| 2004/0247074 | A1 | 12/2004 | Langton | 378/54 |
| 2005/0010106 | A1 | 1/2005 | Lang et al. | 600/425 |
| 2005/0015002 | A1 | 1/2005 | Dixon et al. | 600/407 |
| 2005/0078802 | A1 | 4/2005 | Lang et al. | 378/207 |
| 2005/0148860 | A1 | 7/2005 | Liew et al. | 600/410 |
| 2005/0240096 | A1 | 10/2005 | Ackerman et al. | 600/410 |
| 2006/0062442 | A1 | 3/2006 | Arnaud et al. | 382/128 |
| 2006/0210018 | A1 | 9/2006 | Lang | 378/54 |
| 2007/0047794 | A1 | 3/2007 | Lang et al. | 382/132 |
| 2007/0274442 | A1 | 11/2007 | Gregory et al. | 378/54 |
| 2008/0031412 | A1 | 2/2008 | Lang et al. | 378/54 |
| 2008/0058613 | A1 | 3/2008 | Lang et al. | 600/300 |
| 2008/0097794 | A1 | 4/2008 | Arnaud et al. | 705/3 |
| 2008/0219412 | A1 | 9/2008 | Lang | 378/207 |
| 2009/0207970 | A1 | 8/2009 | Lang | 378/38 |
| 2009/0225958 | A1 | 9/2009 | Lang | 378/207 |
| 2010/0014636 | A1 | 1/2010 | Lang et al. | 378/56 |
| 2010/0098212 | A1 | 4/2010 | Lang | |
| 2010/0130832 | A1 | 5/2010 | Lang et al. | |
| 2010/0197639 | A1 | 8/2010 | Lang et al. | |

FOREIGN PATENT DOCUMENTS

| | | |
|---|---|---|
| DE | 198 53 965 | 5/2000 |
| DE | 19853965 | 5/2000 |
| EP | 0 314 506 | 5/1989 |
| EP | 0 678 191 | 10/1995 |
| EP | 0 797 952 | 10/1997 |
| EP | 0797952 A1 | 10/1997 |
| EP | 0570936 | 8/2000 |
| EP | 1 069 395 | 1/2001 |
| EP | 1 230 896 | 8/2002 |
| EP | 1230896 | 8/2002 |
| EP | 1 349 098 | 1/2003 |
| EP | 1283492 | 2/2003 |
| EP | 1357480 | 10/2003 |
| EP | 1 424 650 | 2/2004 |
| EP | 1 598 778 | 11/2005 |
| GB | 2 023 920 | 1/1980 |
| JP | 62-266053 | 5/1986 |
| JP | 62 266053 | 11/1987 |
| JP | 05 099829 | 4/1993 |
| JP | 08 186762 | 7/1996 |
| JP | 10 145396 | 5/1998 |
| JP | 10-262959 | 10/1998 |
| JP | 11 069136 | 3/1999 |
| JP | 11 112877 | 4/1999 |
| JP | 2002 045722 | 2/2000 |
| JP | 2000 126168 | 5/2000 |
| JP | 2000 139889 | 5/2000 |
| JP | 2002/45722 | 8/2000 |
| JP | 2003230557 | 2/2002 |
| WO | WO 94/12855 | 6/1994 |
| WO | WO 95/14431 | 6/1995 |
| WO | WO 99/08597 | 2/1999 |
| WO | WO 99/45371 | 9/1999 |
| WO | WO 99/45845 | 9/1999 |
| WO | WO 99/52331 | 10/1999 |
| WO | WO 00/33157 | 6/2000 |
| WO | WO 00/72216 | 11/2000 |
| WO | WO 01/38824 | 5/2001 |
| WO | WO 01/63488 | 8/2001 |
| WO | WO 01/65449 | 9/2001 |
| WO | WO 02/17789 | 3/2002 |
| WO | WO 02/22014 | 3/2002 |
| WO | WO 02/30283 | 4/2002 |
| WO | WO 02/096284 | 12/2002 |
| WO | WO 03/071934 | 9/2003 |
| WO | WO 03/073232 | 9/2003 |
| WO | WO 03/088085 | 10/2003 |
| WO | WO 2004/019256 | 3/2004 |
| WO | WO 2004/025541 | 3/2004 |
| WO | WO 2004/062495 | 7/2004 |
| WO | WO 2004/086972 | 10/2004 |
| WO | WO 2004/096048 | 11/2004 |
| WO | WO 2005/027732 | 3/2005 |
| WO | WO 2006/033712 | 3/2006 |
| WO | WO 2006/034018 | 3/2006 |
| WO | WO 2008/034101 | 3/2008 |

OTHER PUBLICATIONS

Hedström et al., "Biochemical Bone Markers and Bone Density in Hip Fracture Patients," *Acta Orthop Scand.* 71(4):409-413 (2000).

Barker, Richard, "Case Method: Entity Relationship Modeling" (Computer Aided Systems Engineering), *Addision-Wesley Pub. Co., publisher* (1990).

Cann, "Quantitative CT for Determination of Bone Mineral Density: A Review," *Radiology* 166:509-522 (1988).

Cootes, Ph.D., T.F. et al., "Anatomical statistical models and their role in feature extraction," *The British Journal of Radiology, Special Issue 2004*, S133-S139.

Cootes et al., "Statistical models of appearance for medical image analysis and computer vision," *Proc. SPIE Medical Imaging*, 14 pages, 2001.

Cootes, T., "An Introduction to Active Shape Models," *Image Processing and Analysis*, Ch. 7:1-26 (2000).

Crawley, E.O., "In Vivo Tissue Characterization Using Quantitative Computed Tomography: A Review," *Journal of Medical Engineering & Technology* 14(6):233-242 (1990).

Davies et al., "A Minimum Description Length Approach to Statistical Shape Modeling," *IEEE Transaction on Medical Imaging*, vol. 21, pp. 5, 525-537 (May 2002).

Duryea et al., "New radiographic-based surrogate outcome measures for osteoarthritis of the knee," *Osteoarthritis and Cartilage*, vol. 11, pp. 102-110 (Feb. 2003).

Duryea et al., "Trainable rule-based algorithm for the measurement of joint space width in digital radiographic images of the knee," *Medical Physics*, 27(3):580-591 (Mar. 2000).

Eastell et al., "Treatment of postmenopausal Osteoporosis," *New Engl. J. of Med.* 338:736-746 (1988).

Engelman, Kimberly K. et al., "Impact of Geographic Barriers on the Utilization of Mammograms by Older Rural Women", *Journal of the American Geriatrics Society*, vol. 50, No. 1, Jan. 2002, pp. 62-68.

Fleute et al., "Incorporating a statistically based shape model into a system for computer-assisted anterior cruciate ligament surgery," *Medical Image Analysis*, 3(3):209-222 (Sep. 1999).

Fleute et al., "Statistical model registration for a C-arm CT system," *IEEE*, pp. 1667-1670 (Nov. 2001).

Fleute et al., "Nonrigid 3-D/2-D Registration of Images Using Statistical Models," pp. 138-147 (Sep. 9, 1999).

Gilliland et al., "Patterns of Mammography Use among Hispanic, American Indian, and Non-Hispanic White Women in New Mexico, 1994-1997", *American Journal of Epidemiology*, vol. 152, No. 5, Sep. 1, 2000, pp. 432-437.

Gluer et al., "Peripheral Measurement Techniques for the Assessment of Osteoporosis," *Semin Nucl. Med.* 27:229-247 (1997).

Gudmundsdottir, et al. "Verterbral Bone Density in Icelandic Women Using Quantitative Computed Tomography Without an External Reference Phantom," *Osteoporosis Int.* 3:84-89 (1993).

Horn, B. "Closed-form solution of absolute orientation using unit quaternions," *Journal Optical Society of America*, 4(4):629-642 (Apr. 1987).

Ikuta, A., Kumasaka, S., Kashima, I., "Quantitative Analysis Using the Star Volume Method Applied to Skeleton Patterns Extracted with a Morphological Filter," *Journal of Bone and Mineral Metabolism*, pp. 271-277 (Mar. 2000).

Jacobs, et al. "Long-term Bone Mass Evaluation of Mandible and Lumbar Spine in a Group of Women Receiving Hormone Replacement Therapy," *European Journal Oral Science*, ISSN 0909-883, Munksgaard, 104:10-12 (1996).

Jazieh, MD, Abdul Rahman et al., "Mammography Utilization Pattern Throughout the State of Arkansas: A Challenge for the Future", *Journal of community Health*, vol. 26, No. 4, Aug. 2001, pp. 249-255.

Klose, "Teleradiology—A Model for Remote Consultation", *Electromedica*, 66(1): 37-41 (1998).

Kumasaka, S., Kashima, I., "Initial Investigation of Mathematical Morphology for the Digital Extraction of the Skeletal Characteristics of Trabecular Bone," *Departments of Oral Surgery and Oral and Maxillofacial Radiology*, Kanagawa Dental College, Yokosuka, Kanagawa, Japan, pp. 161-168 (Oct. 1996).

Ouyang et al. "Morphometric Texture Analysis of Spinal Trabecular Bone Structure Assessed Using Orthogonal Radiographic Projections", *Med. Phys.*, 25(10):2037-2045 (1998).

Patel et al., "Radiation Dose to the Patient and Operator from a Peripheral Dual X-Ray Absorptiometry System," *Journal of Clinical Densitometry* 2(4):397-401 (1999).

Pharoah, Michael, "X-ray Film, Intensifying Screens, and Grids," (*Excerpt from: Oral Radiology: Principles and Interpretation*), 4th Ed., S.C. White, Publisher: Mosby, Inc., pp. 68-76.

"QUS-2 Calcaneal Ultrasonometer", What's New: Ultrasound, Retrieved from the internet, http://www.metrabio.com/html/_prods/L3-ultrasound-r.ht, 2 pages (Jan. 16, 2001).

Beck et al., "Experimental Testing of a DEXA-Derived Curved Beam Model of the Proximal Femur," *J. Orth. Res.*, vol. 16, No. 3, pp. 394-398 (1998).

Black et al., "An Assessment Tool for Predicting Fracture Risk in Postmenopausal Women" *Osteoporosis Int.*, vol. 12, pp. 519-528 (2001).

Blake et al., "Active Contours; The Application of Techniques from Graphics, Vision, Control Theory and Statistics to Visual Tracking of Shapes in Motion," Title page and Table of Contents pages only, 6 pages (1999).

Bushberg et al., "The Essential Physics of Medical Imaging," Title page and Table of Contents pages only, 3 pages (1994).

Castleman, "Digital Image Processing," Title page and Table of Contents pages only, 9 pages (1996).

Cheal et al., "Role of Loads & Prosthesis Material Properties on the Mechanics of the Proximal Femur After Total Hip Arthroplasty," *J. Orthop. Res.*, vol. 10, No. 3, pp. 405-422 (1992).

Cortet et al., "Bone Microarchitecture and Mechanical Resistance," *Joint Bone Spine*, vol. 68, pp. 297-305 (2001).

Crabtree et al., "Improving Risk Assessment: Hip Geometry, Bone Mineral Distribution and Bone Strength in Hip Fracture Cases and Controls. The EPOS Study," *Osteoporosis Int.*, vol. 13, pp. 48-54 (2002).

Cummings et al., "Bone Density at Various Sites for Prediction of Hip Fractures," *The Lancet*, vol. 341, pp. 72-75 (1993).

Faulkner, "Bone Densitometry: Choosing the Proper Skeletal Site to Measure," *J. Clin. Densitometry*, vol. 1, No. 3, pp. 279-285 (1998).

Gluer, "Quantitative Ultrasound Techniques for the Assessment of Osteoporosis: Expert Agreement on Current Status," *J. Bone Miner. Res.*, vol. 12, No. 8, pp. 1280-1288 (1997).

Grisso et al., "Risk Factors for Falls as a Cause of Hip Fracture in Women. The Northeast Hip Fracture Study Group," *N. Engl. J. Med.*, (Abstract Page Only), 1 page, vol. 324, No. 19 (1991).

Hayes et al. "Biomechanics of Cortical and Trabecular Bone: Implications for Assessment of Fracture Risk," Basic Orthopaedic Biomechanics, 2nd Ed., Ch. 3, pp. 69-111 (1997).

Hayes et al., "Biomechanics of Fracture Risk Prediction of the Hip and Spine by Quantitative Computed Tomography," *Radiologic Clinics of North America*, vol. 29, No. 1, pp. 1-18 (1991).

Hayes et al., "Impact Near the Hip Dominates Fracture Risk in Elderly Nursing Home Residents Who Fall," *Calcif. Tissue Int.* (Abstract Page Only), 1 page, vol. 52, No. 3 (1993).

Hosking et al., "Prevention of Bone Loss with Alendronate in Postmenopausal Women Under 60 Years of Age," *N. Engl. J. Med.*, vol. 338, No. 8, pp. 485-492 (1998).

Jeffcoat et al., "Post-menopausal bone loss and its relationship to oral bone loss", *Periodontology*, vol. 23, pp. 94-102 (2000).

Lam et al., "X-Ray Diagnosis: A Physician's Approach," Title/Copyright pages and Index pages only, 4 pages (1998).

Lang et al., "Osteoporosis—Current Techniques and Recent Developments in Quantitative Bone Densitometry" *Radiologic Clinics of North America*, vol. 29, No. 1, pp. 49-76 (1991).

Marshall et al., "Meta-Analysis of How Well Measures of Bone Mineral Density Predict Occurrence of Osteoporotic Fractures," *Br. Med. J.*, vol. 312, pp. 1254-1259 (1996).

Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).

Njeh et al. "The Role of Ultrasound in the Assessment of Osteoporosis: A Review," *Osteoporosis Int.*, vol. 7, pp. 7-22 (1997).

Njeh et al. "Quantitative Ultrasound: Assessment of Osteoporosis and Bone Status," Title page and Table of Contents pages only, 4 pages (1999).

Pinilla et al., "Impact Direction from a Fall Influences the Failure Load of the Proximal Femur as Much as Age-Related Bone Loss," *Calcified Tissue Int.*, vol. 58, pp. 231-235 (1996).

Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).

Russ, "The Image Processing Handbook," 3rd Edition, North Carolina State Univ., Chapter 7: Processing Binary Images, pp. 494-501 (1998).

Ruttiman et al. "Fractal Dimension from Radiographs of Peridontal Alveolar Bone: A Possible Diagnostic Indicator of Osteoporosis," *Oral Surg., Oral Med., Oral Pathol.*, vol. 74, No. 1, pp. 98-110 (1992).

Sandler et al. "An Analysis of the Effect of Lower Extremity Strength on Impact Severity During a Backward Fall," *J. Bio. Eng.*, vol. 123, pp. 590-598 (2001).

Shrout et al. "Comparison of Morphological Measurements Extracted from Digitized Dental Radiographs with Lumbar and Femoral Bone Mineral Density Measurements in Postmenopausal Women," *J. Periondontal*, vol. 71, No. 3, pp. 335-340 (2000).

Slone et al., "Body CT: A Practical Approach," Title page and Table of Contents pages only, 4 pages (1999).

Southard et al., "Quantitative Features of Digitized Radiographic Bone Profiles," *Oral Surg., Oral Med., Oral Pathol.*, vol. 73, No. 6, pp. 751-759 (1992).

Southard et al., "The Relationship Between the Density of the Alveolar Processes and that of Post-cranial Bone," *J. Dent. Res.*, vol. 79, No. 4, pp. 964-969 (2000).

Stout et al., "X-Ray Structure Determination: A Practical Guide," 2nd Ed., Title page and Table of Contents pages only, 4 pages (1989).

Svendsen et al. "Impact of Soft Tissue on In-Vivo Accuracy of Bone Mineral Measurements in the Spine, Hip, and Forearm: A Human Cadaver Study," *J. Bone Miner. Res.*, vol. 10, No. 6, pp. 868-873 (1995).

Tothill et al., "Errors due to Non-Uniform Distribution of Fat in Dual X-Ray Absorptiometry of the Lumbar Spine," *Br. J. Radiol.*, vol. 65, pp. 807-813 (1992).

Van den Kroonenberg et al., "Dynamic Models for Sideways Falls from Standing Height," *J. Bio. Eng.*, vol. 117, pp. 309-318 (1995).

Verhoeven et al., "Densitometric Measurement of the Mandible: Accuracy and Validity of Intraoral Versus Extraoral Radiographic Techniques in an In Vitro Study," *Clin. Oral Impl. Res.*, vol. 9, pp. 333-342 (1998).

White et al., "Alterations of the Trabecular Pattern in the Jaws of Patients with Osteoporosis," *Oral Surg., Oral Med., Oral Pathol., Oral Radiol., and Endod.*, vol. 88, pp. 628-635 (1999).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

International Searching Authority, International Search Report—Appl. No. PCT/US 02/017024, dated Jul. 22, 2002 (2 pages).

International Searching Authority, International Preliminary Examination Report—Appl. No. PCT/US 02/017024, dated Mar. 7, 2003 (3 pages).

European Patent Office, EPO Communication—Application No. 02 739 519.3, dated Dec. 11, 2006 (5 pages).

European Patent Office, EPO Communication—Application No. 02 739 519.3, dated Dec. 20, 2007 (4 pages).

Geraets et al., A New Method for Automatic Recognition of the Radiographic Trabecular Pattern, J. Bone Min. Res., vol. 5, No. 3 (1990), 7 pages.

* cited by examiner

METHODS TO DIAGNOSE TREAT AND PREVENT BONE LOSS

CROSS REFERENCE TO RELATED APPLICATIONS

This application is related to U.S. Provisional Patent Application Ser. No. 60/293,898, and U.S. Provisional Patent Application Ser. No. 60/293,489, both filed on May 25, 2001, from which priority is claimed under 35 USC §119(e)(1), and which applications are incorporated herein by reference in their entireties.

TECHNICAL FIELD

The invention relates generally to methods for diagnosing, screening, prognosing, and treating diseases. More particularly, the present invention relates to a method for diagnosing, screening or prognosing changes in bone loss, bone architecture or bone formation in humans or animals, and for determining the severity and cause of the disease by mathematically combining morphological data with metabolic data obtained using biomarkers.

BACKGROUND

Osteoporosis is a major public health issue caused by a reduction in bone mineral density in mature bone and results in fractures after minimal trauma. The most common fractures occur in the vertebrae, distal radius (Colles' fracture) and hip. An estimated one-third of the female population over age 65 will have vertebral fractures, caused in part by osteoporosis. Moreover, hip fractures are likely to occur in about one in every three woman and one in every six men by extreme old age.

Two distinct phases of bone loss have been identified. One is a slow, age-related process that occurs in both genders and begins at about age 35. This phase has a similar rate in both genders and results in losses of similar amounts of cortical and cancellous bone. Cortical bone predominates in the appendicular skeleton while cancellous bone is concentrated in the axial skeleton, particularly the vertebrae, as well as in the ends of long bones. Osteoporosis caused by age-related bone loss is known as Type II osteoporosis.

The other type of bone loss is accelerated, seen in post-menopausal women and is caused by estrogen deficiency. This phase results in a disproportionate loss of cancellous bone, particularly trabecular bone. Osteoporosis due to estrogen depletion is known as Type I osteoporosis. The main clinical manifestations of Type I osteoporosis are vertebral, hip and Colles' fractures. The skeletal sites of these manifestations both contain large amounts of trabecular bone. Bone turnover is usually high in Type I osteoporosis. Bone resorption is increased but there is inadequate compensatory bone formation. Osteoporosis has also been related to corticosteroid use, immobilization or extended bed rest, alcoholism, diabetes, gonadotoxic chemotherapy, hyperprolactinemia, anorexia nervosa, primary and secondary amenorrhea, transplant immunosuppression, and oophorectomy.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) that then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from the use of corticosteroids or immunosuppressors.

The diagnosis and management of bone related disease, such as osteoporosis, typically requires information about bone turnover and bone mass. Determinations of bone turnover have historically been performed utilizing standard serum, urine and/or sweat laboratory tests including fasting calcium/creatinine, hydroxyproline, alkaline phosphatase and/or osteocalcin/bone growth protein utilizing standard high pressure liquid chromatography (HPLC) techniques. To illustrate, whenever bone formation occurs (calcium deposition) or bone resorption occurs (calcium breakdown), various chemical reactions occur within the body that elevate the presence of certain indicators in the blood and urine suggesting changes in the calcium/bone mineral status. Biomarkers, however, typically lack information on the severity or stage of a disease and, additionally, on the morphological condition of an organ or tissue.

Recently, several new bone specific assays have been developed which enable bone turnover to be evaluated with an ELISA/EMIT immunoassay format. Descriptions of these immunoassay formats can be found in U.S. Pat. Nos. 5,973,666, 5,320,970, 5,300,434 and 5,140,103. The labeling for the new assays utilize a biochemical marker to quantify bone resorption and/or formation and provides information on bone turnover.

For diagnosis of bone diseases, U.S. Pat. No. 6,210,902 describes detecting collagen breakdown products in serum or urine by using two or more immunoassays, and forming a ratio between the concentration of one fragment and a second fragment to form an index to determine the rate of bone resorption. In another method of forming an index of biomarker results, U.S. Pat. No. 5,962,236 obtains a ratio of free lysyl pyridinoline cross-links and creatinine content to form a urinary index of bone resorption to diagnose bone disease. Further, the use of two or more biomarkers to diagnose a disease, where a neural network is first trained and the trained neural network is then used to analyze the experimental data to produce a diagnostic value is disclosed in U.S. Pat. Nos. 6,306,087 and 6,248,063.

Bone mass determinations, on the other hand, have been traditionally performed by using various x-ray based techniques including single and dual-photon absorptiometry (SPA and DPA), quantitative computed tomography (QCT), and dual-energy absorptiometry (DXA). Imaging tests such as x-rays, ultrasound, computed tomography and MRI can provide detailed information about the morphological condition of an organ or a tissue and on the severity or the stage of a disease process. However, such imaging techniques typically lack information on the metabolic activity of various tissues and organs and, in diseased states, cannot give an estimate of the rate of progression or the prognosis of a disease.

U.S. Pat. No. 5,785,041 describes a computer system for displaying biochemical data with data from densitometric bone measurement to determine whether bone formation or bone resorption is occurring.

Thus, there remains a need for methods and devices for diagnosing, prognosticating and monitoring of osteoporosis by combining the information provided by imaging tests with the information provided by biomarkers.

SUMMARY

The present invention provides novel methods for the diagnosis of diseases, particularly bone related diseases, where using a combination of several independent measurements or tests provides for greater diagnostic power.

In one aspect, the invention includes using a mathematical function to relate the level of one or more biomarkers with a numerical value relating to one or more imaging descriptors comprising predetermined features from images defining bone disease characteristics to obtain a test value, and comparing the test value with a control value, wherein a test value which differs from the control value by a predetermined amount is indicative of bone disease.

These and other aspects of the present invention will become evident upon reference to the following detailed description and attached drawings. In addition, various references are set forth herein which describe in more detail certain procedures or compositions, and are therefore incorporated by reference in their entirety.

DETAILED DESCRIPTION OF THE INVENTION

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa: Mack Publishing Company, 1990); Carey and Sundberg *Advanced Organic Chemistry* $3^{rd}$ *Ed.* (Plenum Press) Vols A and B (1992).

All publications, patents and patent applications cited herein, whether supra or infra, are hereby incorporated by reference in their entirety.

I. Definitions

In describing the present invention, the following terms will be employed, and are intended to be defined as indicated below.

By "bone loss" is meant an imbalance in the ratio of bone formation to bone resorption resulting in less bone than desirable in a patient. Bone loss may result from osteoporosis, bone fractures, osteotomy, periodontitis, or prosthetic ingrowth. Bone loss may also result from secondary osteoporosis that includes glucocorticoid-induced osteoporosis, hyperthyroidism-induced osteoporosis, immobilization-induced osteoporosis, heparin-induced osteoporosis or immunosuppressive-induced osteoporosis. Bone loss can be monitored, for example, using bone mineral density measurements described below.

By "increased bone accretion" is meant that bone accumulation in a subject. Such increased bone accretion is determined herein by measuring bone mineral density (BMD). For example, bone accretion can be determined using an animal model, such as an ovariectomized mouse, dog and the like. The animal is administered the test compound and bone mineral density (BMD) measured in bones that are normally depleted in Type I or Type II osteoporosis, such as bones of the appendicular and/or axial skeleton, particularly the spine including the vertebrae, as well as in the ends of long bones, such as the femur, midradius and distal radius. Several methods for determining BMD are known in the art. For example, BMD measurements may be done using, e.g., dual energy x-ray absorptiometry or quantitative computed tomography, and the like. (See, the examples.) Similarly, increased bone formation can be determined using methods well known in the art. For example, dynamic measurements of bone formation rate (BFR) can be performed on tetracycline labeled cancellous bone from the lumbar spine and distal femur metaphysics using quantitative digitized morphometry (see, e.g., Ling et al., *Endocrinology* (1999) 140:5780-5788. Alternatively, bone formation markers, such as alkaline phosphatase activity (see, e.g., Farley et al., *Calcif. Tissue Int.* (1992) 50:67-73) and serum osteocalcin levels (see, e.g., Taylor et al., *Metabolism* (1988) 37:872-877 and Baylink et al., $10^{th}$ Annual Congress of Endocrinology, San Francisco, Calif. (1996) Abstract P1-945), can be assessed to indirectly determine whether increased bone formation has occurred.

As used herein, the terms "treat" or "treatment" are used interchangeably and are meant to indicate a postponement of development of bone loss symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, and/or encouraging bone growth.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The term "biomarker" encompasses any molecule having altered (e.g., reduced or elevated) levels when a particular disease or condition in a subject is present as compared a normal (non-diseased) subject. Non-limiting examples of suitable biomarkers include polynucleotides (e.g., genes, a piece of DNA, a piece of RNA, an oligonucleotide); polypeptides (e.g., enzymes, etc.); lipids; a component of a membrane; a component of an organelle; oligo- or polysaccharides; metals; and/or an element that is naturally occurring in a mammal including a human in a physiologic or a diseased state. The presence, absence and/or amount of a biomarker in a tissue or a bodily fluid can be indicative of a diseased state in a tissue or can be used to assess the metabolic activity of normal or diseased tissue or can be used to prognosticate disease state. Alterations in the concentration of a biomarker in a tissue or a bodily fluid, e.g., an increase or a decrease above or below the normal range expected under physiologic conditions in said tissue or bodily fluid, can be indicative of a diseased state in a tissue or can be used to assess the metabolic activity of normal or diseased tissue or can be used to prognosticate a diseased state in a tissue. Serial changes in the concentration of a biomarker in a tissue or a bodily fluid, e.g., an increase or a decrease in the concentration of said biomarker between two or more time points T1 and T2 in said tissue or bodily fluid, can be indicative of a diseased state in a tissue or can be used to assess the metabolic activity of normal or diseased tissue or can be used to prognosticate a diseased state in a tissue. Biomarkers can also be used to monitor response to a therapeutic intervention. A biomarker can be measured by obtaining tissue samples such as pieces of a mucosal membrane or by obtaining samples of a bodily fluid.

The term "biomarker test" includes a test that assesses (quantitatively or qualitatively) the concentration (amount), presence and/or serial changes in the concentration of a biomarker in a tissue or a bodily fluid. Bodily fluid includes saliva, sputum, nasal secretions, sweat, urine, blood, plasma, serum, synovial fluid, ascites, peritoneal fluid, fluid in a cyst, fluid in an abscess, cerebrospinal fluid, pleural effusions, and pericardial effusions. It is contemplated that the method may also be used, for example, on saliva and sweat. The body fluid may be used as it is, or it may be purified prior to analysis. The purification of the bodily fluids may be accomplished using a number of standard procedures, including, but not limited to, cartridge adsorption and elution, molecular sieve chromatography, dialysis, ion exchange, alumina chromarography, hydroxyapatite chromatography, and combinations thereof.

The term "imaging test" includes, but is not limited to, x-ray based techniques, for example, conventional film based x-ray films, digital x-ray images, single and dual x-ray absorptiometry, and radiographic absorptiometry; ultrasound including broadband ultrasound attenuation measurement and speed of sound measurements; computed tomography; nuclear scintigraphy; SPECT; positron emission tomography and MRI. One or more of these imaging tests may be used in the methods described herein, for example in order to obtain certain information (e.g., morphological) about one or several tissues such as bone including bone mineral density and curvature of the subchondral bone, cartilage including biochemical composition of cartilage, cartilage thickness, cartilage volume, cartilage curvature, marrow including marrow composition, synovium including synovial inflammation, lean and fatty tissue, and thickness, dimensions and volume of soft and hard tissues. The information, which is preferably expressed as a numerical value, is also referred to as "imaging descriptors." The imaging test can be performed with use of a contrast agent, such as Gd-DTPA in the case of MRI.

The term "osteoporosis" includes a condition of generalized skeletal fragility in which bone strength is sufficiently weak that fractures occur with minimal trauma, often no more than is applied by routine daily activity. Its primary manifestations are a reduction in bone mass, measured usually as bone mineral density (BMD) and disruption of the normal skeletal micro-architecture. BMD at any time in adult life reflects the peak investment in bone mineral at skeletal maturity minus that which has been subsequently lost. In some cases, low BMD represents failure to achieve adequate bone mass at skeletal maturity. In other cases, it represents loss of bone.

II. General Overview

The present invention provides, among other things, methods for combining results obtained from assessment of one or more morphological parameters characteristic of a disease with information regarding metabolic, functional, or physiological parameters to evaluate disease status and to provide a prognosis of disease. In particular, for bone diseases, the present invention combines one or more imaging descriptors with one or more biomarker tests using a mathematical function in order to diagnose and/or prognose bone disease. The combining of the two different types of data provides an index that is relevant to the diagnosis of the disease. The imaging descriptors provide information on, for example, bone mineral density, bone structure, and/or the size, shape and invasiveness of the lesion. The biomarker tests provide information on, for example, the rate of growth (or extension) of the lesion. One or more of the imaging descriptors are mathematically manipulated (e.g., divided by or multiplied by the measured level of the biomarker) to derive a diagnostic and/or prognostic index.

The methods described herein may be used, for example, to treat defects resulting from disease of the cartilage (e.g., osteoarthritis), bone damage and/or degeneration due to overuse or age. The invention allows, among other things, a health practitioner to evaluate and treat such defects. Thus, the methods of the invention provide for improved and more specific diagnosis of diseases, and provide for faster determination on the treatment type needed as well as treatment efficacy.

III. Imaging Descriptors

The imaging descriptors provide static assessment of one or more morphological parameters, such as local thickness for cartilage, BMD or structure for bone. The imaging descriptors thus provide data on the characteristics of the bone, such as bone mass, bone density, local thickness of the bone, structure of the bone, thickness of the cartilage, percent cartilage surface diseased, and the like.

When the imaging descriptors pertain to bone mass, a change in the bone mass can typically be measured by four widely available methods known to those skilled in the art, including single photon absorptometry, dual photon absorptometry (DPA), dual-energy x-ray absorptometry (DXA), and quantitative computed tomography quantitative computed tomography (CAT scan). These methods are used to measure mineral content in the bone, and some are relatively selective for certain bones or trabecular versus cortical bone. Other methods for obtaining information concerning bone density and vitality that may reveal information useful in the diagnosis of various diseases including osteopenia, osteoporosis, and arthritis, include magnetic resonance imaging (MRI) and positron emission tomographic (PET) techniques. Radiographic absorptometry (RA) is a method for non-invasive measurement of bone mineral x-rays of the hand.

In another aspect, the imaging test can be performed on any x-ray, for example a dental x-ray obtained in the mandible or maxilla, x-ray of an extremity such as a hand or a calcaneus, a hip x-ray, a spinal x-ray or any other x-ray to obtain a measurement of bone mineral density. The x-ray (e.g., mandible, maxilla) can be analyzed to obtain a measurement bone mineral density, and the analysis can be performed with the help of a calibration phantom or an external standard included on the x-ray image. The calibration phantom or an external standard can be included on the x-ray image or can be scanned separately. The x-ray can also be used to assess bone structure, e.g. trabecular thickness and spacing, trabecular connectivity, or cortical thickness. See, for example, International Publications PCT/US01/26913 and PCT/US01/32040, incorporated by reference herein in their entireties.

In another aspect, imaging descriptors providing quantitative information on the bone is derived from the measurement of the bone density. The density of the bone can be measured by ultrasound to measure broadband ultrasound attenuation values and speed of sound to determine bone density. However, other types of densitometric systems are also contemplated. For example, the densitometric bone measuring system may use x-rays to measure bone density. An example of an x-ray based densitometric bone measuring system using a pencil beam to measure bone density is described in U.S. Pat. No. 4,811,373.

In another aspect of the invention, imaging descriptors providing quantitative information on the bone is derived from an x-ray image. In other aspects, the quantitative information is densitometric information, for example bone mineral density or density of selected soft-tissues or organs. Alternatively, the quantitative information is information on the morphology of a structure, for example information on the two-dimensional arrangement of individual components forming said structure or information on the three-dimensional arrangement of individual components forming said structure. In any of the methods described herein, the structure can be bone and the information can be, for example, information on trabecular thickness, trabecular spacing and/or estimates of the two- or three-dimensional architecture of the trabecular network. Further, in any of the methods described herein, quantitative information can be derived with use of an external standard, for example a calibration phantom of known x-ray density. (e.g., a calibration phantom is included with the structure to be imaged on the x-ray image).

In another aspect, the quantitative information derived from the x-ray image includes one or more parameters relating to the acquisition of the x-ray image (e.g,. x-ray tube voltage, x-ray energy, x-ray tube current, film-focus distance, object-film distance, collimation, focal spot size, spatial resolution of the x-ray system, filter technique, film focus distance, correction factor(s) or combinations thereof), for instance to improve the accuracy of the quantitative information.

Preferably the x-ray images include accurate reference markers, for example calibration phantoms for assessing bone mineral density of any given x-ray image. Thus, in certain aspects, methods that allow accurate quantitative assessment of information contained in an x-ray such as x-ray density of an anatomic structure or morphology of an anatomic structure are used to obtain the imaging descriptors.

An x-ray image can be acquired using well-known techniques from any local site. For example, in certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging. If the x-ray image was captured using conventional x-ray film, the x-ray can be digitized using any suitable scanning device. The digitized x-ray image can then be transmitted over the network, e.g. the internet, into a remote computer or server. It will be readily apparent that x-ray images can also be acquired using digital acquisition techniques, e.g. using phosphorus plate systems or selenium or silicon detector systems, the x-ray image information is already available in digital format. In this case the image can be transmitted directly over the network, e.g. the Internet, or alternatively, it can be compressed prior to transmission.

Preferably, when an x-ray of an anatomic structure or a non-living object is acquired a calibration phantom is included in the field of view. Any suitable calibration phantom can be used, for example, one that comprises aluminum or other radio-opaque materials. U.S. Pat. No. 5,335,260 describes other calibration phantoms suitable for use in assessing bone mineral density in x-ray images. Examples of other suitable calibration reference materials can be fluid or fluid-like materials, for example, one or more chambers filled with varying concentrations of calcium chloride or the like.

It will be readily apparent that a calibration phantom can contain several different areas of different radio-opacity. For example, the calibration phantom can have a step-like design, whereby changes in local thickness of the wedge result in differences in radio-opacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

Alternatively, the calibration reference may be designed such that the change in radio-opacity is from periphery to center (for example in a round, ellipsoid, rectangular of other shaped structure). As noted above, the calibration reference can also be constructed as plurality of separate chambers, for example fluid filled chambers, each including a specific concentration of a reference fluid (e.g., calcium chloride).

Any shape can be used including, but not limited to, squares, circles, ovals, rectangles, stars, crescents, multiple-sided objects (e.g., octagons), irregular shapes or the like, so long as their position is known to correlate with a particular density of the calibration phantom. In preferred embodiments, the calibration phantoms described herein are used in 2D planar x-ray imaging.

Since the density and attenuation of the calibration phantom are both known, the calibration phantom provides an external reference for measuring the density of the anatomic structure or non-living object to be measured. One of skill in the art will easily recognize other applications for use of calibration phantoms in x-ray imaging in view of the teachings herein.

Curvature and/or thickness measurements of bone or other tissue can also be obtained using any suitable techniques, for example in one direction, two directions, and/or in three dimensions. Non-limiting examples of imaging techniques suitable for measuring thickness and/or curvature (e.g., of cartilage and/or bone) include the use of x-rays, magnetic resonance imaging (MRI), computed tomography scanning (CT, also known as computerized axial tomography or CAT), and ultrasound imaging techniques. (See, also, International Patent Publication WO 02/22014; U.S. Pat. No. 6,373,250 and Vandeberg et al. (2002) *Radiology* 222:430-436).

In certain embodiments, CT or MRI is used to assess tissue, bone and any defects therein, for example articular cartilage and cartilage lesions, to obtain information on cartilage degeneration and provide morphologic information about the area of damage. Specifically, changes such as fissuring, partial or full thickness cartilage loss, and signal changes within residual cartilage can be detected using one or more of these methods. For discussions of the basic NM principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement, (RARE) imaging, gradient echo acquisition in the steady state, (GRASS), and driven equilibrium Fourier transform (DEFT) imaging, to obtain information on cartilage, see WO 02/22014. Thus, the measurements may be three-dimensional images obtained as described in WO 02/22014. Three-dimensional internal images, or maps, of the cartilage alone or in combination with a movement pattern of the joint can be obtained. In addition, imaging techniques can be compared over time, for example to provide up to date information on the size and type of repair material needed.

In another aspect, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. In other embodiments, for example if no cartilage remains, the curvature of the articular surface can be measured to design and/or shape the repair material. Further, both the thickness of the remaining cartilage and the curvature of the articular surface can be measured to determine the percent of cartilage surface that is diseased.

Alternatively, or in addition to, imaging techniques, measurements and/or samples can be taken of bone or other tissue intraoperatively during arthroscopy or open arthrotomy. At least one, preferably two or more of these measurements can then be used to provide the data for the morphological parameters.

VI. Biomarker Parameters

Biomarkers of bone disease include any products produced or given off during normal or abnormal growth and/or death of bone and may be used to determine normal, healthy conditions as well as disease states. Non-limiting examples of suitable biomarkers include calcium, hydroxyproline, alkaline phosphatase, procollagen Type I and its cleavage products, osteocalcin, and bone collagen peptides that include crosslinked amino acids. The crosslinked amino acids include pyridinoline, hydroxy lysyl pyridinoline, lysyl pyridinoline, substituted pyridinolines, n-telopeptide, and the peptides that contain these cross-linked amino acids. Current methods used to monitor the presence, progress of treatment, or disease state for metabolic bone diseases require the measurement of biomarkers of bone metabolism found in bodily fluids. Examples of these detection methods are shown in U.S. Pat. Nos. 5,283,197; 4,973,666; and 5,140,103.

The biomarkers are detected in any suitable sample, for example, tissue or body fluids including but not limited to urine, blood, serum, plasma, sweat, saliva and synovial fluid. The sample (e.g., fluid or tissue) may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

The biomarker(s) to be measured will be selected depending on the type of disease, particularly the type of bone disease, to be detected. One or more biomarkers can be selected so that it is characteristic of the disease exhibited by the patient. For example, the preferred biomarkers predictive of bone resorption are n-telopeptides and pyridinole. These biomarkers are indicative of resorption and are present in the bodily fluids in amounts that are detectable and indicative of resorption bone diseases. Thus, the measurement of these biomarkers can provide an indication of the metabolic bone disease, and can be of use in monitoring the progress of medical treatment intended to reduce the loss of bone density found in these diseases.

Osteoporosis and osteopenia provide other examples of diseases for which suitable biomarkers are known. Examples of biomarkers, which can be detected separately or together show characteristic changes in the presence of osteoporosis include: calcium, phosphate, estradiol (follicular, mid-cycle, luteal, or post-menopausal), progesterone (follicular, mid-cycle, luteal, mid-luteal, oral contraceptive, or over 60 years), alkaline phosphatase, percent liver-ALP, and total intestinal-ALP. Typically, after measuring the amount of one or more of these biomarkers, a diagnosing clinician compares the measurements to a normal reference range to determine weather a patient has undergone some bone loss.

Biomarkers typically monitored for bone resorption associated with Paget's disease includes hydroxyproline. Paget's disease, a metabolic bone disorder in which bone turnover is greatly increased. Hydroxyproline is an amino acid largely restricted to collagen, is the principal structural protein in bone and all other connective tissues, and is excreted in urine. The excretion rate of hydroxyproline is known to be increased in certain conditions, particularly in Paget's disease. Therefore, urinary hydroxyproline can be used as an amino acid marker for collagen degradation. U.S. Pat. No. 3,600,132 discloses a process for the determination of hydroxyproline in body fluids such as serum, urine, lumbar fluid and other intercellular fluids in order to monitor deviations in collagen metabolism. The method correlates hydroxyproline with increased collagen anabolism or catabolism associated with pathological conditions such as Paget's disease, Marfan's syndrome, osteogenesis imperfecta, neoplastic growth in collagen tissues and in various forms of dwarfism. Additionally, bone resorption associated with Paget's disease has been monitored by measuring small peptides containing hydroxyproline, which are excreted in the urine following degradation of bone collagen.

Other biomarkers of collagen degradation that have been measured by art known methods includes hydroxylysine and its glycoside derivatives, the cross-linking compound 3-hydroxypyridinium in urine as an index of collagen degradation in joint diseases (Wu and Eyre, Biochemistry 23:1850 (1984) and Black et al., Annals of the Rheumatic Diseases 48:641-644 (1989)) where the peptides from body fluids are hydrolyzed and the presence of individual 3-hydroxypyridinium residues is subsequently detected.

A particularly useful biomarker for determining quantitative bone resorption of type II and type III coliagens involves quantitating in a body fluid the concentration of telopeptides that have a 3-hydroxypyridinium cross-link and that are derived from collagen degradation. Telopeptides are cross-linked peptides having sequences that are associated with the telopeptide region of, for example, type II and type III collagens and which may have cross-linked to them a residue or peptide associated with the collagen triple-helical domain. The telopeptides can have fewer amino acid residues than the entire telopeptide domains of type II and type III collagens, and they may comprise two peptides linked by a pyridinium cross-link and further linked by a pyridinium cross-link to a residue or peptide of the collagen triple-helical domain. Methods for quantitating in a body fluid the concentration of telopeptides having a 3-hydroxypyridinium cross-link derived from bone collagen resorption are known in art. For example, GB patent application No. 2,205,643 reports that the degradation of type III collagen in the body can be quantitatively determined by measuring the concentration of an N-terminal telopeptide from type III collagen in a body fluid.

Typically, the patient's body fluid is contacted with an immunological binding partner specific to a telopeptide having a 3-hydroxypyridinium cross-link derived from type II or type III collagen. The body fluid may be used as is or purified prior to the contacting step. This purification step may be accomplished using a number of standard procedures, including cartridge adsorption and elution, molecular sieve chromatography, dialysis, ion exchange, alumina chromatography, hydroxyapatite chromatography, and combinations thereof.

The biomarker telopeptide having a 3-hydroxypyridinium cross-linked can alternatively be quantitated by fluorometric measurement of a body fluid containing the biomarker. The fluorometric assay can be conducted directly on a body fluid without further purification. However, for certain body fluids, particularly urine, it is preferred that purification of the body fluid be conducted prior to the fluorometric assay. This purification step consists of dialyzing an aliquot of a body fluid such as urine against an aqueous solution thereby producing partially purified peptide fragments retained within the nondiffusate (retentate). The nondiffusate is then lyophilized, dissolved in an ion pairing solution and adsorbed onto an affinity chromatography column. The chromatography column can be washed with a volume of ion pairing solution and, thereafter, the peptide fragments are eluted from the column with an eluting solution. These purified peptide fragments can then be hydrolyzed and the hydrolysate resolved chromatographically. Chromatographic resolution may be conducted by either high-performance liquid chromatography or microbore high performance liquid chromatography.

In another method, the assaying of type I, II and III collagen fragments in urine is performed by an inhibition ELISA (enzyme linked immunosorbent assay) by metering off a sample of urine and contacting the sample with a telopeptides and with an antibody, which is immunoreactive with the telopeptide. The telopeptide can be immobilized on a solid support, and the antibody is raised against the telopeptide. The combined reagents and sample are incubated, and a peroxidase-conjugated antibody is added. After another incubation, a peroxidase substrate solution is added. Following short final incubation, the enzyme reaction is stopped, and the absorbance is measured at about 450 nm and compared with a standard curve obtained with standard solutions by the same procedure.

Other examples of biomarkers which may be sued include osteocalcin, also known as bone GLA protein of BGP, procollagen type I, bone alkaline phosphatase and total alkaline phosphatase. Suitable methods for the determination of these markers can be found, for example, in Delmas, P. D., et al., J. Bone Min. Res. 1:333-337 (1986).

Thus, biomarker parameters characteristic of bone disease can be detected by performing, for example, a quantitative in-vitro diagnostic test on a bodily fluid sample such as blood, urine, saliva or sweat. However, other techniques or methods may also be utilized for obtaining one or more of the biomarker parameter, including, for example, a solid-phase immunoassay technique, a western blotting technique and fluorescent microscopy technique. Various types of assays, such as chemical, enzymatic, and immunochemical assays, may be used to obtain the biochemical data. Chemical assays may detect, for example, phosphorous and/or calcium. Enzymatic assays may detect, for example, the enzyme action of alkaline phosphatase. Immunochemical assays may detect biologic compounds, such as pyridinoline, hydroxy lysyl pyridinoline, lysyl pyridinoline, substituted pyridinolines, and n-telopeptide, by monoclonal or polyclonal antibodies or specific receptor proteins.

V. Mathematical Functions

The imaging descriptors are combined with the biomarker parameters using a mathematical function. The mathematical function can be division, product, sum, logarithmic function, exponential function, and the like. In certain aspects of the invention, one or more of the mathematical functions can be used in combination.

In one aspect of the invention, biochemical assays can be performed to measure bone disease and imaging descriptors can be obtained on the affected area. The results of the biochemical assay can then be divided by the results from the imaging descriptors to provide a ratio or an index. By creating the index between the two assays, information about the disease, such as, for example, the progression of the disease can be obtained.

In another aspect, a plurality of biomarkers associated with one or more selected bone disease can be derived and can be combined with a plurality of imaging descriptors. For example, for osteoporosis, calcium, phosphate, and alkaline phosphatase can be measured, as well as the thickness of the bone and bone density. The sum of the measured concentration of the biomarkers can then be multiplied by the sum of the imaging descriptors to derive an index.

In another aspect, one or more of the selected biomarkers and one or more of the selected imaging descriptors can be measured over a period of time and the relationship between the two can then be statistically analyzed. The time period can be seconds, minutes, hours, days, or months or any interval therebetween. The biochemical and morphological data can be, for example, obtained at 0, 1, 2, 3, 5, 7, 10, 15, and 24 hours. The rate of change of the morphological parameters can then be compared with the rate of change of the biochemical data as a function of time. Alternatively, the biochemical data can be correlated with the morphological data, where the slope of the correlation serves as an index. The regression statistical analysis of the data can be performed using the STATA™ v3.1 (Stata Corporation, College Station, Tex.) statistical analysis software program, or any other commercially available statistical analysis software. The regression analysis can be applied to every independent parameter measured, for example, biomarkers chosen, bone thickness, BMD, and the like. Statistical significance may consist of p values $\leq 0.05$, and can be used to determine which of the parameters are aggregately significant in the prediction of progression of the disease.

In another aspect of the invention, the results can be compared by combining them mathematically to form a numerical index, such as by taking their ratio. A ratio formed between the morphological data and the biochemical data provides an index which is dependent on the progression of the bone disease and which therefore can be used for diagnostic purposes for disorders associated with bone diseases.

The methods of the present invention are sensitive and accurate thereby allowing a practitioner to diagnose bone related diseases promptly, and follow and assess with greater speed and efficiency the treatment of these bone diseases with various therapies. For example, when a clinician evaluates the imaging descriptors and the biomarker parameters individually, the onset of bone related diseases may not be diagnosed promptly. The clinician normally compares these values for a particular patient with the range of reference values generated for the same age group, and the measured values may fall within this reference range. Thus, the measured test results for the patient may fall within the expected values for these tests even though the patient has developed early stages of a bone disease, leading to a misdiagnosis. In contrast, when the results of the two or more independent tests are mathematically combined in accordance with the present invention, the resultant values provide for greater diagnostic power. The methods of the present invention thus provide for early diagnosis of diseases. Similarly, the progression of the disease or the effectiveness of the treatment for the disease can be evaluated with greater speed.

In another aspect of the invention, a database of the ratios is created for a particular bone disease. For example, a particular numerical index result can be associated with particular patient types. This may be done by subjecting a range of samples of known disease type to the methods described above and building up a database of index results. One may then identify the index of an unknown sample as being typical of a particular class of sample previously tested.

Thus, the combined analysis of results of the imaging test and the results of the biomarker test can provide an improved assessment of the patient's prognosis. For example, the combined analysis of the results of the imaging tests and the results from the biomarker tests can help determine the patient's current bone health or degree of osteopenia or osteoporosis or dental disease more accurately. In addition, the combined analysis provides an estimate for the rate of progression of osteopenia or osteoporosis or dental disease more accurately.

In another aspect of the invention, the results of an imaging test to assess bone mineral density or bone structure and architecture can be combined with the results of a biomarker test whereby the combination of the results can help select the most appropriate form of therapy, e.g., therapy with an anabolic drug rather than an anti-resorptive drug and vice versa. For example, the combination of the imaging and biomarker results can indicate that a patient's osteopenia or osteoporosis or dental disease is largely the result of bone resorption, an anti-resorptive drug such as a bisphosphonate can be prescribed. Alternatively, if the combination of results indicate that a patient's osteopenia or osteoporosis or dental disease is largely the result of lack of bone formation an anabolic drug, e.g., parathyroid hormone or one of its derivatives, can be prescribed.

VI. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Measuring Bone Mineral Density

An image of a body part is obtained using one or more of the following techniques: dual x-ray absorptiometry (DXA) (Eastell et al. (1998) *New Engl J. Med* 338:736-746); quantitative computed tomography (QCT) (Cann (1988) *Radiology* 166:509-522); peripheral DXA (pDXA) (Patel et al. (1999) *J Clin Densitom* 2:397-401); peripheral QCT (pQCT) (Gluer et. al. (1997) *Semin Nucl Med* 27:229-247); radiographic absorptiometry (RA) (Gluer et. al. (1997) *Semin Nucl Med* 27:229-247); standard x-ray technology; and quantitative ultrasound (QUS) (Njeh et al. "Quantitative Ultrasound: Assessment of Osteoporosis and Bone Status" 1999, Martin-Dunitz, London England). The image may be digitized and stored electronically.

Bone mineral density is then determined by analyzing the image as described in International Publications PCT/US01/26913 and PCT/US01/32040. Data on bone mineral density may be taken at multiple time points from the same patient and may be some or all of the results may be stored in a database.

EXAMPLE 2

Serum and Urine Bone Biomarkers

Serum and urine biomarkers provide an economical and practical way to measure formation and resorption without invasive surgery. Serum and urine bone biomarkers are assayed at baseline and at 1, 3, 6, 12, 18, and 24 months. Serum total ALP (bone formation), ACP and tartrate-resistant ACP (TRAP, bone resorption), calcium, and phosphorus are measured using a Cobas Fara Chemistry Analyzer (Roche Diagnostics, Nutley, N.J.) (Carlson, et al., 1992; Jayo et al., 1995; Jerome, et al., 1994). Serum BGP (bone turnover) assays are performed using an established radioimmunoassay. Bone resorption is measured using FDA-approved N-telopeptide collagen excretion markers (Osteomarke, Ostex, Seattle, Wash.).

EXAMPLE 3

Combining Imaging and Biomarkers

The value of N-telopeptide at each time point measured in Example 2 is divided by the bone mineral density value obtained in Example 1. The ratio thus obtained is compared to a database that contains a ratio from non-diseased patients. The ratio is then used to determine whether the patient's osteopenia is predominantly the result of lack of bone formation.

EXAMPLE 4

Treatment Based on Combining Imaging and Biomarkers

The patient of Example 3 diagnosed as having osteopenia due to the lack of bone formation is treated with parathyroid hormone, an anabolic drug. The imaging and biomarker tests described in Examples 1 and 2 are repeated, and the results combined according to Example 3. The index obtained is used to follow the effectiveness of the treatment with the drug. The differences in the index value at different time points can be used to assess the efficacy of treatment of the patient for osteoporosis.

Thus, novel methods for diagnosing and prognosing diseases, such as bone loss diseases, are disclosed. Although preferred embodiments of the subject invention have been described in some detail, it is understood that obvious variations can be made without departing from the spirit and the scope of the invention as defined by the appended claims.

What is claimed is:

1. A method for diagnosis of osteoarthritis using a computer system, the method comprising:
   obtaining data associated with one or more biomarkers and data associated with one or more imaging descriptors;
   deriving quantitative information from said one or more imaging descriptors and relating it to a numerical value;
   using a mathematical function to combine (i) the level of one or more biomarkers and (ii) the numerical value relating to the quantitative information derived from said one or more imaging descriptors, to obtain a numerical index;
   comparing the numerical index with a database of index results; and
   analyzing whether said numerical index falls within a range of database of index results that is predetermined to be indicative of osteoarthritis.

2. The method of claim 1, wherein the one or more biomarkers are selected from the group consisting of genes, DNA, RNA, oligonucleotides, enzymes, lipids, a component of a membrane, a component of an organelle, oligosaccharides, polysaccharides, metals and combinations thereof.

3. The method of claim 1, wherein the one or more imaging descriptors are selected from the group consisting of cartilage thickness, cartilage volume, biochemical composition of cartilage, curvature of cartilage and combinations thereof.

4. The method of claim 1, wherein the mathematical function is selected from the group consisting of division, product, sum, logarithmic function, exponential function, and combinations thereof.

5. The method of claim 4, wherein the mathematical function is division.

6. The method of claim 4, wherein the mathematical function is product.

7. The method of claim 4, wherein the mathematical function is sum.

8. The method of claim 1, wherein the one or more imaging descriptors is thickness of cartilage.

9. The method of claim 1, wherein the level of one or more biomarkers is determined by immunological assay.

10. The method of claim 1, wherein the computer system includes a network.

11. The method of claim 10, wherein the network is the Internet.

12. The method of claim 1, wherein the computer system includes two or more computers.

13. The method of claim 1, wherein the computer system includes at least one computer and at least one device.

14. The method of claim 1, wherein at least one of the one or more imaging descriptors includes predetermined features from images defining osteoarthritis characteristics.

15. A method for diagnosis of osteoarthritis, the method comprising:
   obtaining information in a computer system associated with one or more biomarkers and information associated with one or more imaging descriptors;
   using a mathematical function to combine (i) information associated with the level of one or more biomarkers and (ii) information associated with a numerical value relating to the one or more imaging descriptors to obtain a numerical index, wherein at least one imaging descriptor pertains to at least one of thickness of cartilage and percent cartilage surface diseased;
   comparing the numerical index with a database of index results; and
   analyzing whether said numerical index falls within the range of database of index results that is predetermined to be indicative of osteoarthritis.

16. The method of claim 15, wherein the one or more imaging descriptors is thickness of cartilage.

17. The method of claim 16, wherein the computer system includes a network.

18. The method of claim 17, wherein the network is the Internet.

19. The method of claim 16, wherein the computer system includes two or more computers.

20. The method of claim 16, wherein the computer system includes at least one computer and at least one device.

21. The method of claim 16, wherein at least one of the one or more imaging descriptors includes predetermined features from images defining osteoarthritis characteristics.

* * * * *